US006266422B1

(12) United States Patent
Ikeda

(10) Patent No.: US 6,266,422 B1
(45) Date of Patent: Jul. 24, 2001

(54) NOISE CANCELING METHOD AND APPARATUS FOR THE SAME

(75) Inventor: Shigeji Ikeda, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 09/015,622

(22) Filed: Jan. 29, 1998

(30) Foreign Application Priority Data

Jan. 29, 1997 (JP) .................................................. 9-014409

(51) Int. Cl.[7] .......................... A61F 11/06; G10K 11/16; H03B 29/00

(52) U.S. Cl. .................... 381/71.11; 381/71.9; 381/94.1; 381/94.7; 708/372

(58) Field of Search ............................ 381/71.11, 71.12, 381/FOR 123, FOR 124, 94.1, 94.2, 94.3, 94.7, 71.1; 708/322

(56) References Cited

U.S. PATENT DOCUMENTS

| | | | |
|---|---|---|---|
| 5,608,804 | 3/1997 | Hirano | 381/71.12 |
| 5,699,424 * | 12/1997 | Hirano | 381/71.11 |
| 5,953,380 * | 9/1999 | Ikeda | 381/94.1 |

FOREIGN PATENT DOCUMENTS

| | | |
|---|---|---|
| 0 661 832 | 7/1995 | (EP) . |
| 0 730 262 | 9/1996 | (EP) . |
| 0 751 619 | 1/1997 | (EP) . |
| 7-202765 | 8/1995 | (JP) . |

OTHER PUBLICATIONS

Widrow et al. "Adaptive Noise Cancelling: Principles and Applications" Proceedings of IEEE 63:1692–1716 (1975).

Nagumo et al. "A Learning Method for System Identification" *IEEE Transactions on Automatic Control* 12:282–287 1967.

Widrow, B., et al., "Adaptive Noise Cancelling: Principles and Applications," Proceedings of the IEEE, vol. 63, No. 12, pp. 1692–1716 (Dec. 1, 1975).

* cited by examiner

*Primary Examiner*—Xu Mei
(74) *Attorney, Agent, or Firm*—Foley & Lardner

(57) ABSTRACT

A noise canceler of the present invention is of the type including an adaptive filter for generating a pseudo noise signal, subtracting the pseudo noise signal from a received signal to thereby output an error signal, and sequentially correcting the filter coefficient of the filter in accordance with the error signal. A second adaptive filter produces a second pseudo noise signal and a second error signal. A first and a second power mean circuit each calculates the signal power of the respective signal. A divider performs division with the resulting two kinds of signal power, so that a signal-to-noise power ratio is estimated. A comparator compares the estimated signal-to-noise power ratio and a delayed version of the same and outputs greater one of them as an extended signal-to-noise power ratio. A step size output circuit corrects, based on the extended signal-to-noise power ratio and reference noise signal power output from a power mean circuit, a step size used to adaptively vary the filter coefficient of the first adaptive filter.

11 Claims, 5 Drawing Sheets

NOISE CANCELING METHOD AND APPARATUS FOR THE SAME

BACKGROUND OF THE INVENTION

The present invention relates to a noise canceling method and an apparatus for the same and, more particularly, to a noise canceling method for canceling, by use of an adaptive filter, a background noise signal introduced into a speech signal input via a microphone, a handset or the like, and an apparatus for the same.

A background noise signal introduced into a speech signal input via, e g., a microphone or a handset is a critical problem when it comes to a narrow band speech coder, speech recognition device and so forth which compress information to a high degree. Noise cancelers for canceling such acoustically superposed noise components include a biinput noise canceler using an adaptive filter and taught in B. Widrow et al. "Adaptive Noise Cancelling: Principles and Applications", PROCEEDINGS OF IEEE, VOL. 63, NO. 12, DECEMBER 1975, pp. 1692–1716 (Document 1 hereinafter).

The noise canceler taught in Document 1 includes an adaptive filter for approximating the impulse response of a noise path along which a noise signal input to a reference input terminal to propagate toward a speech input terminal. The noise canceler generates a pseudo noise signal corresponding to a noise signal component introduced into the speech input terminal and subtracts the pseudo noise signal from a received signal input to the speech input terminal (combination of a speech signal and a noise signal), thereby suppressing the noise signal.

The filter coefficient of the above adaptive filter is corrected by determining a correlation between an error signal produced by subtracting the estimated noise signal from the main signal and a reference signal derived from the reference signal microphone. Typical of an algorithm for such coefficient correction, i.e., a convergence algorithm is "LMS algorithm" describe in Document 1 or "LIM (Learning Identification Method) algorithm" described in IEEE TRANSACTIONS ON AUTOMATIC CONTROL, VOL. 12, NO. 3, 1967, pp. 282–287 (Document 2 hereinafter).

A conventional noise cancellation principle will be described with reference to FIG. 5. As shown, a speech uttered by a talker is acoustoelectrically transformed to a speech signal by, e.g., a microphone located in the vicinity of the talker's mouth. The speech signal, containing a background noise signal, is applied to a speech input terminal 1. A signal output from a microphone remote from the talker by acoustoelectrical transduction substantially corresponds to the background noise signal input to the speech input terminal 1 and is applied to a reference signal input terminal 2.

The combined speech signal and background noise signal applied to the speech input terminal 1 (referred to as a received signal hereinafter) is fed to a delay circuit 3. The delay circuit 3 delays the received signal by a period of time of Δdt1 and delivers the delayed received signal to a subtracter 5. The subtracter 5 is used to satisfy the law of cause and effect. The delay Δt1 is usually selected to be about one half of the number of taps of an adaptive filter 4.

On the other hand, the noise signal input to the reference input terminal 2 is fed to the adaptive filter 4 as a reference noise signal. The adaptive filter 4 filters the noise signal to thereby output a pseudo noise signal. The pseudo noise signal is fed to the subtracter 5. The subtracter 5 subtracts the pseudo noise signal from the delayed received signal output from the delay circuit 3, thereby cancelling the background noise signal component of the received signal. The received signal free from the background noise signal component is fed out as an error signal.

The adaptive filter 4 sequentially updates its filter coefficient on the basis of the reference noise signal input via the reference input terminal 2, the error signal fed from the subtracter 5, and a step size α selected for coefficient updating beforehand. To update the filter coefficient, use may be made of an "LMS (Least Minimum Square) algorithm" taught in Document 1 or the "LIM" taught in Document 2.

Assume that the received signal input via the speech input terminal 1 contains a speech signal component s(k) (k being an index representative of time) and a noise signal component n(k) to be canceled. Also, assume that the delay Δt1 assigned to the delay circuit 3 is zero for the simplicity of description. Then, a received signal y(k) input to the subtracter 5 via the speech input terminal 1 is expressed as:

$$y(k)=s(k)+n(k) \qquad \text{Eq. (1)}$$

The adaptive filter 4, receiving a reference noise signal x(k) via the reference input terminal 2, so operates as to output a pseudo noise signal r(k) corresponding to the noise signal component n(k) included in the above Eq. (1). The subtracter 5 subtracts the pseudo noise signal r(k) from the received signal y(k) to thereby output an error signal e(k). Let additional noise components not to be canceled be neglected because they are far smaller than the speech signal component s(k). Then, the error signal e(k) may be expressed as:

$$e(k)=s(k)+n(k)-r(k) \qquad \text{Eq. (2)}$$

How the filter coefficient is updated will be described hereinafter, assuming the LMS algorithm described in Document 1. Let the j-th coefficient of the adaptive filter 4 at a time k be wj(k). Then, the pseudo noise signal r(k) output from the filter 4 is produced by:

$$r(k)=\sum_{j=0}^{N-1}\omega j(k)\cdot x(k-j) \qquad \text{Eq. (3)}$$

where N denotes the number of steps of the filter 4.

By applying the pseudo noise signal r(k) given by the Eq. (3) to the Eq. (2), there can be produced the error signal e(k). With the error signal e(k), it is possible to determine a coefficient wj(k+1) at a time (k+1):

$$wj(k+1)=wj(k)+\alpha\cdot e(k)\cdot x(k-j) \qquad \text{Eq. (4)}$$

where α is a constant referred to as a step size and used as a parameter for determining the converging time of the coefficient and the residual error after convergence.

As for the LIM scheme taught in Document 2, the filter coefficient is updated by use of the following equation:

$$\omega j(k+1)=\omega j(k)+\frac{\mu\cdot e(k)\cdot x(k-j)}{\sum_{m=0}^{N-1}x^2(k-m)} \qquad \text{Eq. (5)}$$

where $\mu$ denotes the step size relating to the LIM scheme. Specifically, in the LIM scheme, the step size is inversely proportional to the mean power of the reference noise signal x(k) input to the adaptive filter so as to implement more stable convergence than the LMS algorithm.

A greater step size $\alpha$ in the LMS algorithm or a greater step size $\mu$ in the LIM scheme promotes rapid convergence because the coefficient is corrected by a greater amount. However, when any component obstructing the updating of the coefficient is present, the greater amount of updating is noticeably influenced by such a component and increases the residual error. Conversely, a smaller step size reduces the influence of the above obstructing component and therefore the residual error although it increases the converging time. It follows that a trade-off exists between the "converging time" and the "residual error" in the setting of the step size.

Now, the object of the adaptive filter 4 for noise cancellation is to generate the pseudo signal component r(k) of the noise signal portion n(k). Therefore, to produce an error signal for updating the filter coefficient, a difference between n(k) and r(k), i.e., a residual error (n(k)−r(k)) is essential. However, the error signal e(k) contains the speech signal component −s(k), as the Eq. (2) indicates. The speech signal component s(K) turns out an interference signal component noticeably affecting the operation for updating the adaptive filter 4.

To reduce the influence of the speech signal component s(k) which is an interference signal for the adaptive filter 4, the step size for updating the coefficient of the filter 4 may be reduced. This, however, would slow down the convergence of the filter 4.

Japanese Patent Laid-Open Publication No. 7-202765 (Document 3 hereinafter) discloses a convergence algorithm for an adaptive filter applicable to an echo canceler and giving considering to the influence of the above interference signal. This convergence algorithm is such that the step size of an adaptive filter is controlled on the basis of an estimated interference signal level so as to obviate the influence of the interference signal. A system identification system described in Document 3 and using an adaptive filter determines a section where the pseudo generated signal output from the adaptive filter 4 is small, and estimates an interference signal level in such a section.

The pseudo generated signal mentioned above corresponds to the pseudo noise signal r(k) particular to a noise canceler or corresponds to a pseudo echo signal particular to an echo canceler. Assume that the adaptive filter is converged, and that the pseudo noise signal r(k) output from the filter is zero or negligibly small, compared to s(k), in a given section. Then, because the noise signal n(k) to be estimated by the adaptive filter is also zero, the Eq. (2) is rewritten as:

$$e(k) \approx s(k) \quad \text{Eq. (6)}$$

That is, the interference signal component s(k) is produced as an error signal e(k). It follows that if a section where the above assumption is satisfied can be identified, it is possible to estimate the level of the interference signal s(k). When the interference signal level is high, a decrease in the residual error ascribable to the interference signal can be obviated if the step size is relatively reduced.

To estimate the level of the interference signal s(k) by applying the system of Document 3 to a noise canceler, it is necessary that a section where the pseudo noise signal r(k) output from the adaptive filter be zero (or small), i.e., where the noise signal n(k) itself is zero (or small) be present. As for an echo canceler, because the adaptive filter estimates an echo signal, i.e., a speech, a soundless section naturally exits and allows an interference signal to be stably estimated. However, as for a noise canceler, the adaptive filter estimates a noise signal to be canceled, so that a soundless section does not always exist. This is true with, e.g., noise ascribable to an air conditioner or a vehicle engine. In this condition, the adaptive filter cannot estimate the level of the interference signal.

SUMMARY OF THE INVENTION

It is therefore an object of the present invention to provide a noise canceler capable of reducing the converging time and reducing distortion after convergence (residual error) even when noise is constantly present.

In accordance with the present invention, a noise canceling method includes the steps of inputting a reference noise signal received via a reference input terminal to a first adaptive filter to thereby generate a first pseudo noise signal in accordance with a filter coefficient assigned to the first adaptive filter, causing a first subtracter to subtract the pseudo noise signal from a received signal input via a speech input terminal and consisting of a speech signal and a background noise signal to thereby generate a first error signal, and sequentially correcting the filter coefficient of the first adaptive filter on the basis of the first error signal. The first subtracter outputs a received signal free from noise. The method is characterized by the following. The reference noise signal is input to a second adaptive filter to thereby generate a second pseudo noise signal in accordance with a preselected filter coefficient. A second subtracter is caused to subtract the second pseudo noise signal from the received signal to thereby output a second error signa. Mean power of the second error signal and mean power of the second pseudo error signal are detected to calculate a signal-to-noise power ratio. The signal-to-noise power ratio and a delayed signal-to-noise power ratio delayed by a preselected period of time relative to the signal-to-noise power ratio are compared so as to output greater one of them as an extended signal-to-noise power ratio. The filter coefficient of the first adaptive filter is adaptively varied in accordance with the value of the extended signal-to-noise power ratio and the mean power of the reference noise signal.

Also, in accordance with the present invention, a noise canceler includes a first delay circuit for delaying by a first period of time a received signal input via a speech input terminal and consisting of a speech signal and background noise. A second delay circuit delays a reference noise signal input via a reference input terminal by a second period of time. A first adaptive filter receives a delayed reference noise signal from the second delay circuit and a first error signal and outputs a first pseudo noise signal in accordance with a filter coefficient. A first subtracter subtracts the first pseudo noise signal from a delayed received signal output from the first delay circuit to thereby feed the resulting difference to the first adaptive filter as the first error signal, and outputs a received signal free from noise to an output terminal. An estimator receives the reference noise signal via the reference input terminal and the received signal via the speech input terminal to thereby estimate a signal-to-noise power ratio of the received signal. A third delay circuit delays an estimated value output from the estimator by a third period of time. A signal-to-noise power ratio estimator compares a delayed estimated value output from the third delay circuit and the estimated value output from the estimator, and outputs greater one of them as an estimated value of an extended signal-to-noise power ratio. A step size output circuit outputs, based on the power of the reference noise signal and the extended signal-to-noise power ratio, a step sized for determining a correction value of the filter coefficient of the first adaptive filter.

BRIEF DESCRIPTION OF THE DRAWINGS

The above and other objects, features and advantages of the present invention will become apparent from the following detailed description taken with the accompanying drawings in which.

DESCRIPTION OF THE PREFERRED EMBODIMENT

Figure 1:
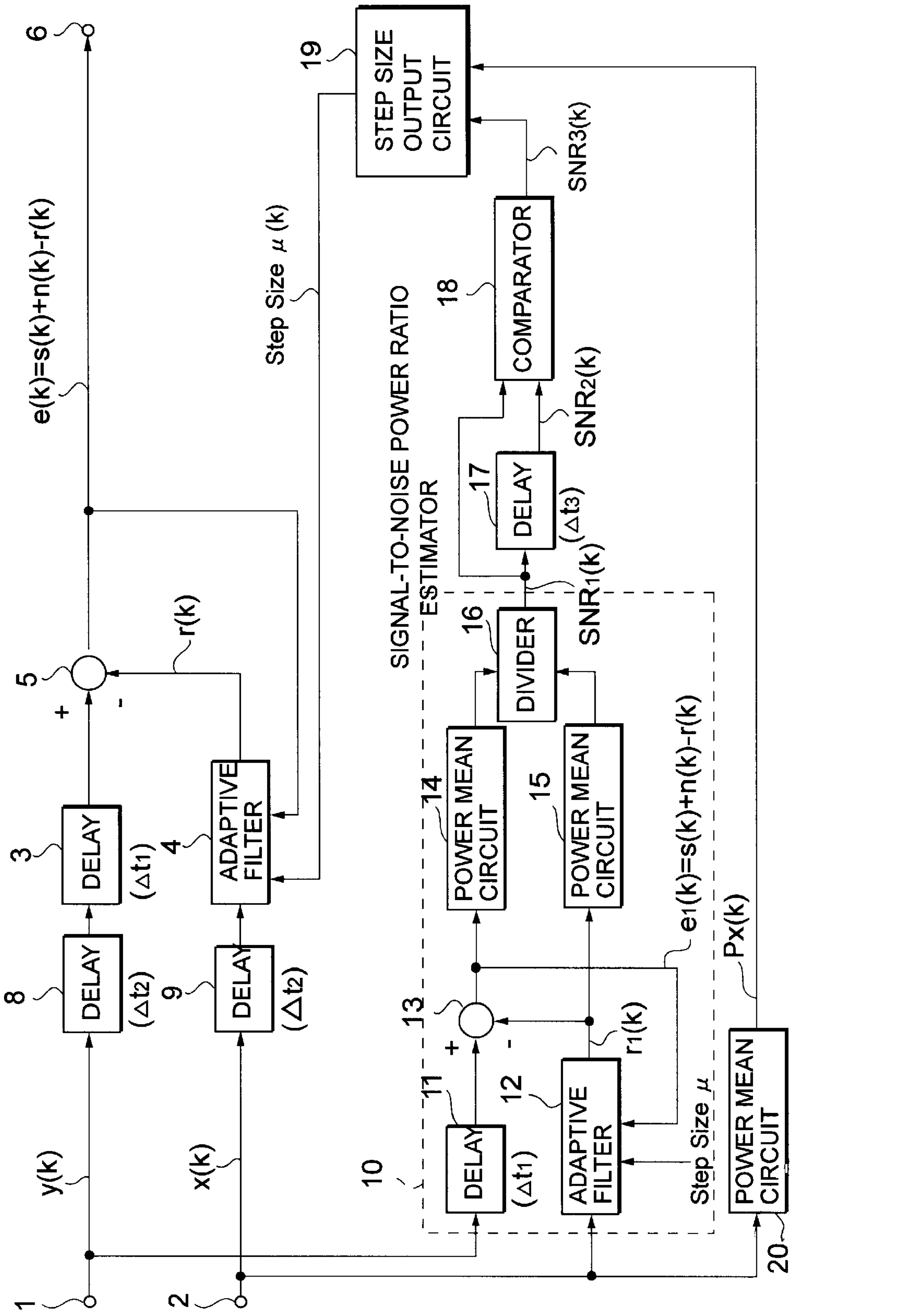
FIG. 1 is a block diagram schematically showing a noise canceler embodying the present invention.
Figure 5:
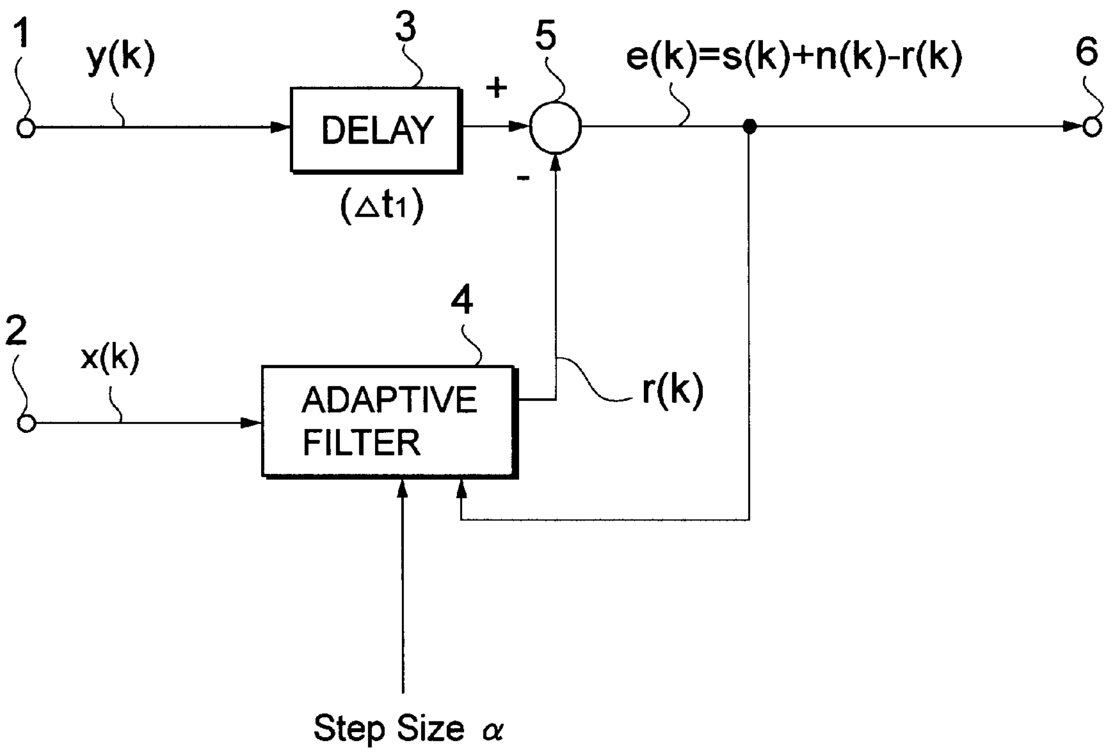
FIG.5 PRIOR ART
FIG. 5 is a schematic block diagram showing a conventional noise canceler.

Referring to FIG. 1 of the drawings, a noise canceler embodying the present invention is shown. In FIG. 1, the same structural elements as the elements shown in FIG. 5 are designated by identical reference numerals. As shown, the noise canceler includes delay circuits 8 and 9, a signal-to-noise power ratio estimator 10, a delay circuit 17, a comparator 18, a step size output circuit 19 and a power mean circuit 20 in order to control the step size of an adaptive filter 4.

The signal-to-noise power ratio estimator 10 includes a delay circuit 11 to which a received signal y(k) is input from a speech input terminal 1. An adaptive filter 12 receives a reference noise signal x(k) via a reference input terminal 2. A subtracter 13 subtracts a pseudo noise signal r1(k) output from the adaptive filter 12 from the output signal of the delay circuit 11. Power mean circuits 14 and 15 respectively average the power of the output signal of the subtracter 13 and the power of the output signal of the adaptive filter 12. A divider 16 divides the output signal of the power mean circuit 14 by the output signal of the power mean circuit 15.

The operation of the signal-to-noise power ratio estimator 10 will be described first. The adaptive filter 12 receives the reference noise signal x(k) via the reference input terminal 2 and outputs a pseudo noise signal r1(k). The delay circuit delays the received signal y(k) by a period of time of Δt1 and serves to satisfy the law of cause and effect like the delay shown in, FIG. 5. The subtracter 13 subtracts the pseudo noise signal output from the adaptive filter 12 from the delayed received signal output from the delay circuit 11, thereby outputting an error signal. The error signal is fed from the subtracter 13 to the adaptive filter 12.

A relatively great step size for updating the coefficient of the adaptive filter 12 is selected in order to promote rapid convergence. Specifically, when the LIM scheme of Document 2 is used as an updating algorithm, a step size $\mu$ of 0.2 to 0.5 is used by way of example.

Assume that a delay Δt1 assigned to the delay circuit 11 is zero, as in the conventional noise canceler. Then, the subtracter 13 outputs an error signal e1(k):

$$e1(k)=y(k)-r1(k) \qquad \text{Eq. (7)}$$

Because the received signal y(k) is the sum of the speech signal s(k) and noise signal n(k) as represented by the Eq. (1), the Eq. (7) is rewritten as:

$$e1(k)=s(k)+n(k)-r1(k) \qquad \text{Eq. (8)}$$

The error signal e1(k) output from the subtracter 13 is fed to the adaptive filter 12 as an error signal for updating the coefficient and is fed to the power mean circuit 14 also. The power mean circuit 14 squares the error signal e1(k) in order to produce its time mean. The square $e1^2(k)$ of the error signal e1(k) is produced by:

$$e1^2(k)=\{s(k)+n(k)-r1(k)\}^2 \qquad \text{Eq. (9)}$$

While the power mean circuit 14 outputs the time mean of the square $e1^2(k)$, assume that the time mean is approximated by an expected value. Then, because the speech signal s(k) and reference noise signal x(k) and therefore the speech signal s(k) and noise signal n(k) are independent of each other, an expected value $E[e1^2(k)]$ is expressed as:

$$E[e1^2(k)]=E[s^2(k)]+E[\{n(k)-r1(k)\}^2] \qquad \text{Eq. (10)}$$

In the Eq. (10), the second member is representative of the residual error component. Considering the fact that rapid convergence is implemented by the relatively great step size, the residual error component attenuates rapidly. Therefore, the following equation holds:

$$E[e1^2(k)]\approx E[s^2(k)] \qquad \text{Eq. (11)}$$

Therefore, as the Eq. (11) indicates, the output signal of the power mean circuit 14 approximates the speech signal power $s^2(k)$.

On the other hand, the power mean circuit 15 squares the pseudo noise signal r1(k) output from the adaptive filter 12 and outputs its time mean. Because the adaptive filter 12 converges rapidly due to the relatively great step size, there holds an equation:

$$r1(k)\approx n(k) \qquad \text{Eq. (12)}$$

It follows that the expected value $E[r1^2(k)]$ of the square $r1^2$ of the pseudo noise signal r1(k) can be approximated by:

$$E[r1^2(k)]\approx E[n^2(k)] \qquad \text{Eq. (13)}$$

Consequently, the output signal of the power mean circuit 15 approximates the noise signal power $n^2(k)$. The divider 16 divides the speech signal power output from the power mean circuit by the noise signal power output from the power mean circuit 15, thereby outputting a signal-to-noise power ratio SNR1.

When the averaging operation of the power mean circuits 14 and 15 is implemented by, e.g., the method of moving average, the calculated power mean values involve a delay of ΔAV dependent on the number of times of averaging with respect to the actual power variation. The illustrative embodiment includes the delay circuits 8 and 9 in order to compensate for the above delay ΔAV. The delay circuit 9 is connected to the input of the adaptive filter 4 in order to delay the reference noise signal by a period of time of At2. The delay circuit 8 is connected to the input of the delay circuit 3 in order to delay the received signal by Δt2.

The delay Δt2 is usually selected to be equal to or greater than ΔAV. Should ΔAV be selected to be greater than Δt2, a change in SNR1 would be detected earlier than the actual SNR of the received signal input to the subtracter 5, extending the SNR1 in the negative direction with respect to time. It is to be noted that the delay circuits 8 and 3 may be implemented as a single delay circuit providing a delay of (Δt2+Δt1).

As stated above, the signal-to-noise power ratio estimator 10 receives the received signal via the speech input terminal 1 and the reference noise signal via the reference signal input terminal 2, causes the adaptive filter 12 to output a pseudo noise signal, detects error signal power and pseudo noise signal power out of, among the others, the pseudo noise signal power output from the adaptive filter 12, and outputs an estimated signal-to-noise power ratio SNR1(k) at a time k on the basis of the above two kinds of power.

The operation of the delay circuits 8, 9 and 17 and that of the comparator 18 are as follows. The delay circuit 17 delays the estimated signal-to-noise power ratio SNR1(k) output from the estimator 10 by a period of time of Δt3(k). The comparator 18 compares the estimated signal-to-noise power ratio SNR1(k) before input to the delay circuit 17 and a delayed estimated signal-to-noise power ratio SNR2(k) output from the delay circuit 17 and outputs greater one of them as an estimated value SNR3(k).

Figures 2A, 2B, 2C:
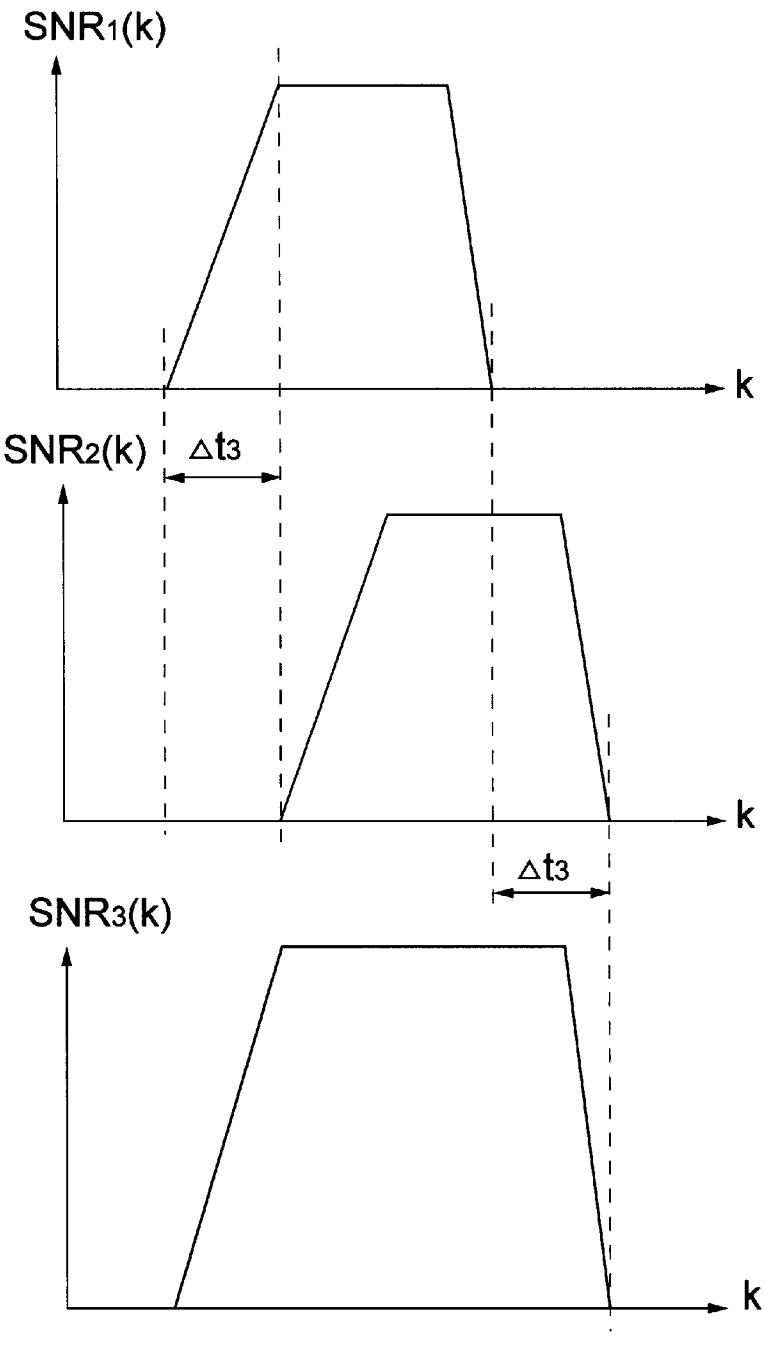
FIGS. 2A–2C demonstrate the extension of a signal-to-noise power ratio with respect to time and effected by the illustrative embodiment.

FIGS. 2A–2C show a relation between the estimated signal-to-noise power ratios SNR1(k) and SRN2(k) and the estimated value SNR3(k). FIG. 2A shows the estimated signal-to-noise power ratio SNR1(k) before input to the delay circuit 17. When the estimated value SNR1(k) is delayed by Δt3 by the delay circuit 17, it turns out the estimated value SNR2(k) shown in FIG. 2B. As a result, the comparator 18 outputs the estimated value SNR3(k) shown in FIG. 2C. It will be seen that the estimated value SNR1(k) is extended by Δt3 in the positive direction with respect to time to turn out the estimated value SNR3(k).

The power mean circuit 20 squares the reference noise signal x(k) so as to output its time mean. This power mean circuit 20 is used to calculate the mean power Px(k) of the reference signal input to a reference noise microphone and thereby determine the absolute amount of noise.

Figure 3:
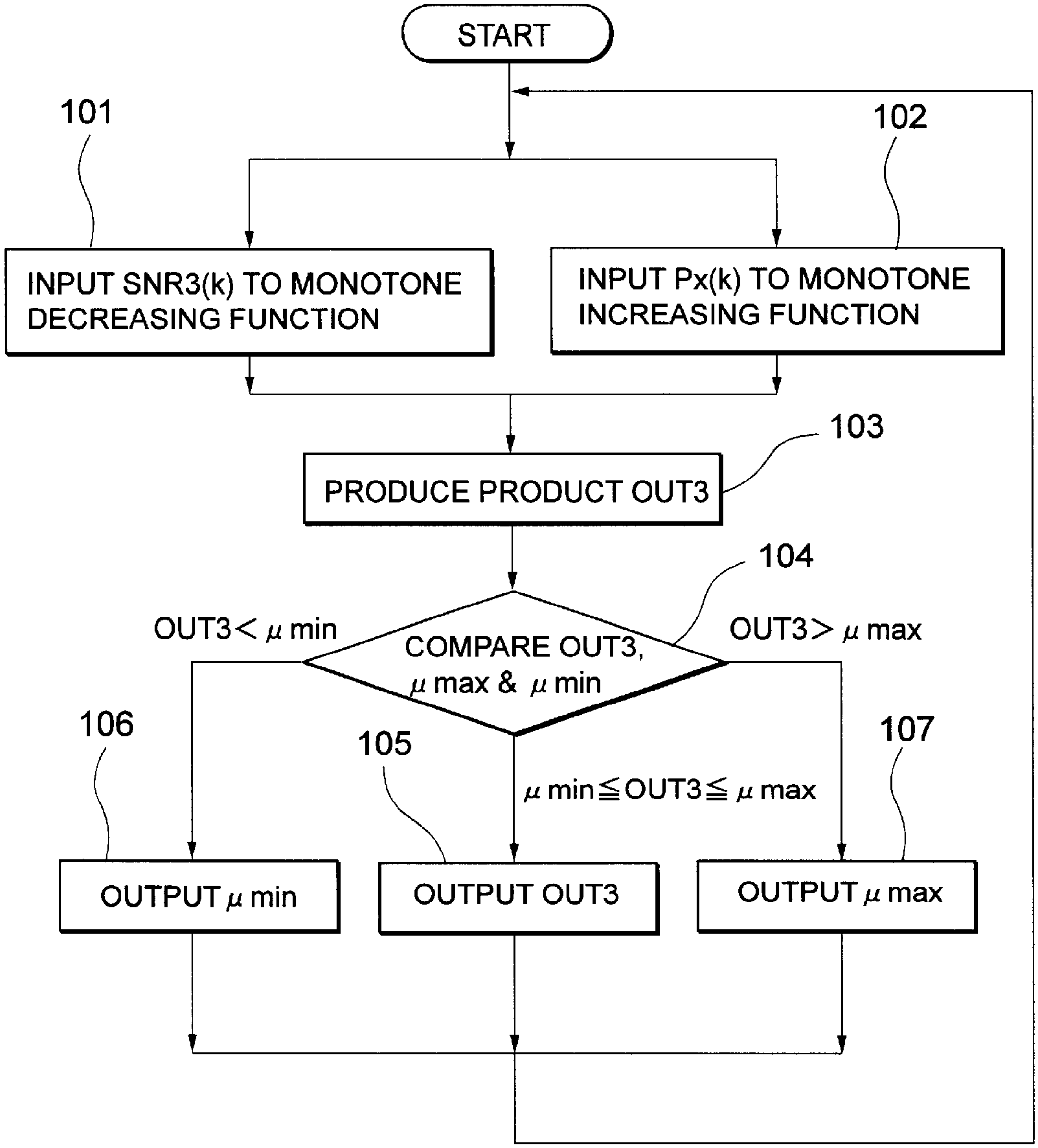
FIG. 3 is a flowchart representative of the operation of a step size output circuit included in the illustrative embodiment.

Reference will be made to FIG. 3 for describing the operation of the step size output circuit 19. First, the estimated signal-to-noise power ratio SNR3(k) output from the comparator 18 is input to a monotone decreasing function (step 101). Assuming that f(·) is the monotone decreasing function for SNR3 (k), then the output OUT1(k) of the function is produced by:

$$\mathrm{OUT1}(k)=f(\mathrm{SNR3}(k)) \quad \text{Eq. (14)}$$

On the other hand, the reference noise signal power Px(k) output from the power mean circuit 20 is input to a monotone increasing function (step 102). Assuming that g(·) is the monotone decreasing function for Px(k), then the output OUT2(k) of the function is produced by:

$$\mathrm{OUT2}(k)=g(Px(k)) \quad \text{Eq. (15)}$$

The outputs OUT1(k) of the monotone decreasing function and the output OUT2(k) of the monotone increasing function are multiplied so as to produce a product OUT3(k) (step 103):

$$\mathrm{OUT3}(k)=\mathrm{OUT1}(k)\cdot\mathrm{OUT2}(k) \quad \text{Eq. (16)}$$

The product OUT3(k) gives a step size $\mu(k)$, as follows:

$$\mu(k)=\mathrm{clip}[\mathrm{OUT3}(k),\ \mu\mathrm{max},\ \mu\mathrm{min}] \quad \text{Eq. (17)}$$

where clip[a, b, c] is a function for setting the maximum value and minimum value and defined as:

$$\mathrm{clip}[a, b, c]=a(c \leqq a \leqq b)$$

$$\mathrm{clip}[a, b, c]=b(a>b)$$

$$\mathrm{clip}[a, b, c]=c(a<c) \quad \text{Eq. (18)}$$

The above procedure is represented by steps 104–107.

Limiting the step size by use of the maximum value $\mu$max and minimum value $\mu$min is desirable for the stable operation of the adaptive filter.

Figure 4A:
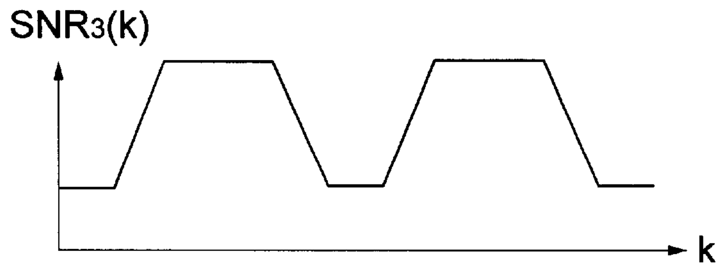
FIGS. 4A–4E show a specific procedure for calculating a step size particular to the illustrative embodiment.
Figure 4B:
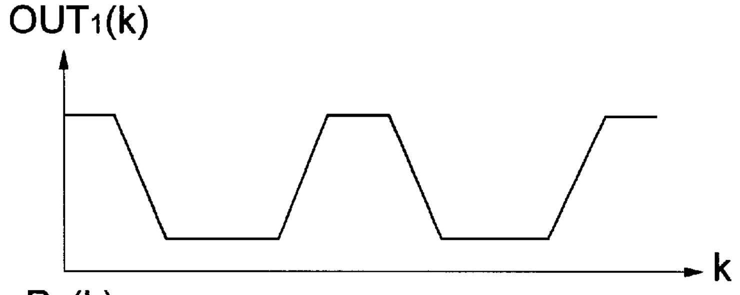

A specific operation of the step size output circuit 19 will be described with reference to FIGS. 4A–4E. FIG. 4A is a graph showing the estimated values SNR3(k) of the extended signal-to-noise power ratio. FIG. 4B shows OUT1(k) produced by inputting SNR3(k) to the monotone decreasing function. Because the function decreases monotonously, OUT1(k) decreases when SNR3(k) increases and increases when SNR3(k) decreases.

Figure 4C:
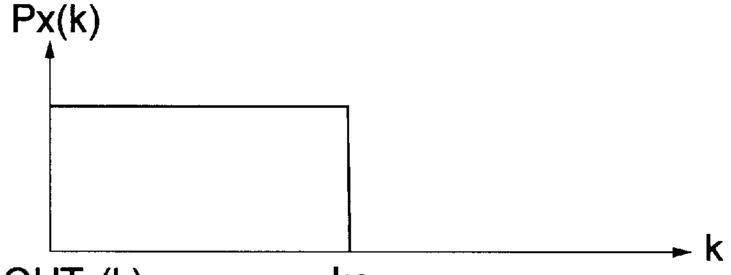
Figure 4D:
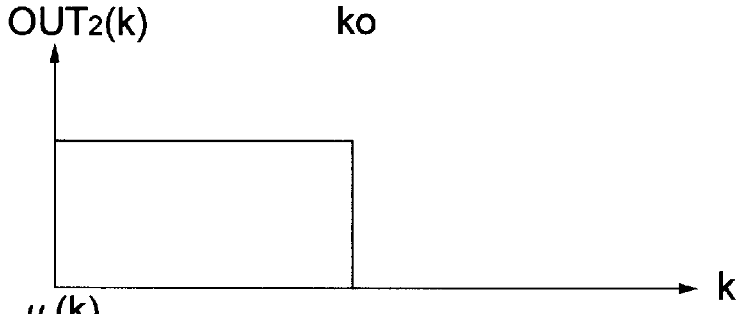

FIG. 4C is a graph showing the reference noise signal power Px(k). In the specific condition shown in FIG. 4C, the reference noise power is zero at a time k0. FIG. 4D shows OUT2(k) produced by inputting Px(k) to the monotonous increasing function. Because the function increases monotonously, OUT2(k) increases and decreases in unison with Px(k).

Figure 4E:
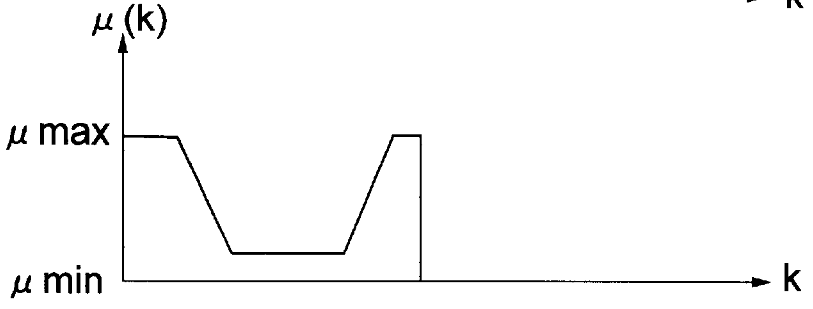

FIG. 4E is a graph showing the step size which is the product of OUT1(k) and OUT2(k) shown in FIGS. 4B and 4D, respectively. As shown, the step size is inversely proportional to SNR3(k) up to the time k0, but is zero after the time k0 because the reference noise power is zero. In this manner, the step size is weighted by the reference noise signal power and therefore does not increase when the reference noise signal power is small. In this manner, the step size output circuit 19 controls the step size for the adaptive filter 4 in accordance with the estimated value SNR3(k) of the extended signal-to-noise power ratio and reference noise signal power Px(k).

As stated above, the illustrative embodiment estimates an SNR value and controls the step size for the adaptive filter 4 in accordance with the estimated SNR value. Therefore, in a section where a speech signal is absent or, if present, far smaller than a noise signal component, the step size can be increased in order to promote rapid convergence without being influence by an interference signal.

On the other hand, in a section where the speech signal component is greater than the noise signal component, the step size can be reduced in order to prevent a residual error from increasing due to an interference signal. Further, the estimated value SNR3(k) of the extended signal-to-noise power ratio and used for step size control is extended in the negative direction by the delay circuits 8 and 9 and in the positive direction by the delay circuit 17 with respective to time. This allows the step size to be reduced before a speech signal and then increased after the speech signal and thereby insures the stable convergence of the adaptive filter.

Moreover, because the step size is weighted by the reference noise signal power, it is prevented from increasing excessively when the amount of noise is absolutely short.

In summary, it will be seen that the present invention provides a noise canceler realizing rapid convergence and reducing a residual error because it determines, based on the estimated value of an extended signal-to-noise power ratio, a relation in size between a speech signal, which is an interference signal component for the updating of the coefficient of an adaptive filter, and a noise signal component to be canceled and controls a step size to be fed to a first adaptive filter in accordance with the determined relation.

What is claimed is:

1. A noise canceling method including the steps of inputting a reference noise signal received via a reference input terminal to a first adaptive filter to thereby generate a first pseudo noise signal in accordance with a filter coefficient assigned to said first adaptive filter, causing a first subtracter to subtract the pseudo noise signal from a received signal input via a speech input terminal and consisting of a speech signal and a background noise signal to thereby generate a first error signal, and sequentially correcting the filter coefficient of the first adaptive filter on the basis of the first error signal, the first subtracter outputting a received signal free from noise, said noise canceling method comprising the steps of:

(a) inputting the reference noise signal to a second adaptive filter to thereby generate a second pseudo noise signal in accordance with a preselected filter coefficient;

(b) causing a second subtracter to subtract said second pseudo noise signal from the received signal to thereby output a second error signal;

(c) detecting mean power of said second error signal and mean power of said second pseudo error signal to thereby calculate a signal-to-noise power ratio;

(d) extending a period of time of said signal-to-noise power ratio to output as an extended signal-to-noise power ratio; and (e) varying the filter coefficient of the first adaptive filter adaptively in accordance with a value of said extended signal-to-noise power ratio and a mean power of the reference noise signal.

2. A method as claimed in claim 1, wherein step (e) comprises:

(f) inputting the value of said extended signal-to-noise power ratio to a preselected monotonously decreasing function to thereby calculate a first function value;

(g) inputting the mean power of the reference noise signal to a preselected monotonously increasing function to thereby calculate a second function value;

(h) multiplying said first function value and said second function value and outputting a resulting product; and (i) outputting, as a step size for determining an amount of correction of the filter coefficient of the first adaptive filter, said product if said product is between a preselected maximum value and a preselected minimum value, or outputting said maximum value if said product is greater than said maximum value, or outputting said minimum value if said product is smaller than said minimum value.

3. A method as claimed in claim 1, wherein a step size for determining a filter coefficient of said second adaptive filter is a constant value.

4. A noise canceler comprising:

first delaying means for delaying by a first period of time a received signal input via a speech input terminal and consisting of a speech signal and background noise;

second delaying means for delaying a reference noise signal input via a reference input terminal by a second period of time;

a first adaptive filter for receiving a delayed reference noise signal from said second delaying means and a first error signal and outputting a first pseudo noise signal in accordance with a filter coefficient;

first subtracting means for subtracting said first pseudo noise signal from a delayed received signal output from said first delaying means to thereby feed a resulting difference to said first adaptive filter as said first error signal, and outputting a received signal free from noise to an output terminal;

estimating means for receiving the reference noise signal via said reference input terminal and the received signal via said speech input terminal to thereby estimate a signal-to-noise ratio of the received signal;

third delaying means for delaying an estimated value output from said estimating means by a third period of time;

extending means for receiving a delayed estimated value output from said third delaying means and said estimated value output from said estimating means, and for outputting a greater one of said delayed estimated value and said estimated value as an estimated value of an extended signal-to-noise power ratio; and step size outputting means for outputting, based on power of the reference noise signal and said extended signal-to-noise power ratio, a step size for determining a correction value of the filter coefficient of said first adaptive filter.

5. A noise canceler as claimed in claim 4, wherein said signal-to-noise power ratio estimating means comprises:

fourth delaying means for delaying the received signal input via said speech input terminal by a fourth period of time;

a second adaptive filter for receiving the reference noise signal from said reference input terminal and a second error signal to thereby output a second pseudo noise signal in accordance with a preselected filter coefficient;

second subtracting means for subtracting said second pseudo noise signal from a delayed received signal output from said fourth delaying means, and feeding a resulting difference to said second adaptive filter as said second error signal;

means for calculating a square mean of said second error signal to thereby output received signal power;

means for calculating a square mean of said second pseudo noise signal to thereby output noise signal power; and means for dividing said received signal power by said noise signal power to thereby output an estimated value of a signal-to-noise power ratio of the received signal.

6. A noise canceler as claimed in claim 4, further comprising:

means for inputting said estimated value of said extended signal-to-noise power ratio to a preselected monotonously decreasing function to thereby output a first function value;

means for inputting said noise signal power to a preselected monotonously increasing function to thereby output a second function value;

means for multiplying said first function value and said second function value to thereby output a resulting product; and means for outputting, as a step size for determining an amount of correction of the filter coefficient of said first adaptive filter, said product if said product is between a preselected maximum value and a preselected minimum value, or ouptutting said maximum value if said product is greater than said maximum value, or outputting said minimum value if said product is smaller than said minimum value.

7. A noise canceler as claimed in claim 4, wherein said second period of time is equal to or longer than a time delay ascribable to a calculation of said estimated value of said signal-to-noise power ratio, and wherein said first period of time is longer than said second period of time.

8. A noise canceler as claimed in claim 5, wherein said fourth period of time is equal to a period of time produced by subtracting said second period of time from said first period of time.

9. A noise canceler as claimed in claim 5, wherein a step size for determining an amount of correction of the filter coefficient of said second adaptive filter is a constant value.

10. A noise canceler comprising:

received signal delaying means for delaying a received signal including a speech signal and a noise signal;

reference noise signal delay means for delaying a reference noise signal;

a first adaptive filter for receiving a delayed reference noise signal from said reference noise signal delay means and a first error signal and outputting a first pseudo noise signal in accordance with a filter coefficient;

first subtracting means for subtracting said first pseudo noise signal from a delayed received signal delivered from said received signal delay means to thereby feed a resultant difference to said first adaptive filter as said first error signal, and outputting a noise-cancelled received signal;

estimating means for estimating a signal-to-noise power ratio based on the reference noise signal and the received signal to thereby deliver a signal-to-noise power ratio estimated signal;

means for extending a period of time of said signal-to-noise power ratio estimated signal to produce an extended signal-to-noise power ratio estimated signal;

step size controlling means for controlling a step size which determines a correction value of the filter coefficient of said first adaptive filter on the basis of said extended signal-to-noise power ratio estimated signal, and noise power detecting means for detecting a noise power of said reference noise signal, wherein said step size controlling means controls said step size on the basis of said noise power in addition to said extended signal-to-noise power ratio estimated signal.

11. A noise canceler comprising:

a first delaying circuit that delays by a first period of time a received signal input via a speech input terminal and consisting of a speech signal and background noise;

a second delay circuit that delays a reference noise signal input via a reference input terminal by a second period of time;

a first adaptive filter for receiving a delayed reference noise signal from said second delay circuit and a first error signal and outputting a first pseudo noise signal in accordance with a filter coefficient;

a first subtracter that subtracts said first pseudo noise signal from a delayed received signal output from said first delay circuit to thereby feed a resulting difference to said first adaptive filter as said first error signal, and outputting a received signal free from noise to an output terminal;

a signal-to-noise power ratio estimator that receives the reference noise signal via said reference input terminal and the received signal via said speech input terminal to thereby estimate a signal-to-noise ratio of the received signal;

a third delay circuit that delays an estimated value output from said estimator by a third period of time;

a comparator that compares a delayed estimated value output from said third delay circuit and said estimated value output from said estimator, and outputs a greater one of said delayed estimated value and said estimated value as an estimated value of an extended signal-to-noise power ratio; and a step size output circuit that outputs, based on power of the reference noise signal and said extended signal-to-noise power ratio, a step size for determining a correction value of the filter coefficient of said first adaptive filter.

* * * * *